United States Patent
Yanai et al.

(10) Patent No.: US 6,829,942 B2
(45) Date of Patent: Dec. 14, 2004

(54) PRESSURE SENSOR

(75) Inventors: Kenichi Yanai, Nisshin (JP); Hiroto Nakatani, Nagoya (JP); Tomoyasu Watanabe, Kariya (JP)

(73) Assignee: Denso Corporation, Kariya (JP)

( * ) Notice: Subject to any disclaimer, the term of this patent is extended or adjusted under 35 U.S.C. 154(b) by 5 days.

(21) Appl. No.: 10/606,893

(22) Filed: Jun. 27, 2003

(65) Prior Publication Data

US 2004/0000195 A1 Jan. 1, 2004

(30) Foreign Application Priority Data

Jun. 27, 2002 (JP) ........................................ 2002-187902

(51) Int. Cl.[7] ................................................. G01L 9/00
(52) U.S. Cl. ............................................ 73/754; 73/716
(58) Field of Search .......................... 73/753, 754, 727, 73/706, 721, 862.041

(56) References Cited

U.S. PATENT DOCUMENTS

| | | | | |
|---|---|---|---|---|
| 5,054,323 A | * | 10/1991 | Hubbard et al. | ............... 73/754 |
| 6,155,120 A | * | 12/2000 | Taylor | ................... 73/862.046 |
| 6,216,545 B1 | * | 4/2001 | Taylor | ................... 73/862.046 |
| 6,216,546 B1 | * | 4/2001 | Bahr | ..................... 73/862.046 |
| 6,388,556 B1 | * | 5/2002 | Imai et al. | ................... 338/114 |
| 6,450,957 B1 | | 9/2002 | Yoshimi et al. | |
| 6,626,046 B2 | * | 9/2003 | Taguchi et al. | ............... 73/753 |
| 6,694,822 B1 | * | 2/2004 | Ganapathi et al. | ............ 73/763 |

FOREIGN PATENT DOCUMENTS

| | | |
|---|---|---|
| JP | A-64-59132 | 3/1989 |
| JP | A-2001-70256 | 3/2001 |
| JP | A-2001-99726 | 4/2001 |

\* cited by examiner

*Primary Examiner*—Edward Lefkowitz
*Assistant Examiner*—Andre Allen
(74) *Attorney, Agent, or Firm*—Posz & Bethards, PLC

(57) ABSTRACT

A pressure sensor includes a pair of base films, a pair of electrodes, a layer of pressure-sensitive resistor, a spacer, and a projection. The electrodes are located between the base films. The layer of pressure-sensitive resistor is located between the base films to be distant from one of the electrodes by a predetermined gap. The spacer is located outside the layer of pressure-sensitive resistor between the base films and used for forming the gap. The projection is located on an outer surface of one of the base films in order to decrease the lowest pressure that can be detected by the pressure sensor. The contact state between the layer of pressure-sensitive resistor and one of the electrodes varies to vary the resistance between the electrodes when a pressure acts on the projection.

17 Claims, 5 Drawing Sheets

PRESSURE SENSOR

CROSS REFERENCE TO RELATED APPLICATION

This application is based on and incorporates herein by reference Japanese Patent Application No. 2002-187902 filed on Jun. 27, 2002.

BACKGROUND OF THE INVENTION

The present invention relates to a pressure sensor that can be used in low load pressure measurement such as pressure distribution measurement of a human body lying on a bed.

A pressure sensor can be used for acquiring living body information such as respiration and pulse of a sleeper. The living body information of a sleeper can be acquired by detecting the movement of the sleeper. The movement of the sleeper is detected by placing a pressure sensor in an article on which the sleeper lies such as a bed and detecting the variation in the pressure exerted on the pressure sensor. However, the output of the pressure sensor includes the output component corresponding to the load based on the sleeper's weight, which provides a relatively high signal level, and the output component corresponding to the load variation based on the minute local movement of the sleeper's body caused by respiration and so on, which provides a relatively low signal level.

Usually, the local movement of the sleeper's body caused by respiration and so on is so small that the load variation based on the local movement is extremely small than the load based on the sleeper's weight. Therefore, the pressure sensor is required to precisely detect the load variation based on the minute local movement. Moreover, the pressure sensor is required to make a subject unconscious of the existence of the pressure sensor.

A proposed pressure sensor is disclosed, for example, in the publication JP-A-2001-99726. The proposed sensor includes: a pair of base films; a pair of electrodes located between the base films; a layer of pressure-sensitive resistor located between the electrodes with a predetermined gap from one of the electrodes or two layers of pressure-sensitive resistor respectively located on the electrodes with a predetermined gap; and a spacer located outside the layer(s) of the pressure-sensitive resistor to form the gap. The contact state between the layer(s) of the pressure-sensitive resistor and the electrodes varies in response to the pressure exerted on the pressure-sensitive resistor through the base films. That is, the pressure is detected on the basis of the variation in the resistance between the electrodes.

In the proposed pressure sensor mentioned above, the base films and the spacer are thinned to permit the contact state between the layer(s) of the pressure-sensitive resistor and the electrodes to vary readily. Therefore, it is possible to precisely detect the load variation based on the minute local movement and to make a subject unconscious of the existence of the pressure sensor.

When living body information such as respiration and pulse of a sleeper is detected using a pressure sensor, a pressure sensor sheet that is made up of a plurality of the proposed pressure sensors has usually been used. In the pressure sensor sheet, the base films of the sensor are commonly used. That is, the plurality of the proposed pressure sensors are formed by arranging electrodes, pressure-sensitive resistors, spacers, and so on between a pair of large base films. With the arrangement, it is possible to stably detect the living body information even if the position of a sleeper varies on the pressure sensor sheet when the sleeper turns.

However, there is a problem with the proposed pressure sensor that the output deviation between the sensors and the output deviation in repeated detections increase because the base films are thinned are thinned in order to decrease the detectable lowest pressure. In addition, the signal level of the sensor output can be affected when the portions of the base films outside the spacers are stretched by the sleeper or the article on which the sleeper lies. As a result, it becomes difficult to maintain a good detection precision. This is especially prominent in the proposed pressure sensor. That is, there is a problem with the proposed pressure sensor that as the detectable lowest pressure decreases, it becomes difficult to maintain a good detection precision.

SUMMARY OF THE INVENTION

The present invention has been made in view of the above aspects with an object to provide a pressure sensor that can be used for a pressure sensor sheet to detect a low pressure with preferably high detection precision.

To achieve the above object, a pressure sensor according to the present invention includes a pair of base films, a pair of electrodes, a layer of pressure-sensitive resistor, a spacer, and a projection. The electrodes are located between the base films. The layer of pressure-sensitive resistor is located between the base films to be distant from one of the electrodes by a predetermined gap. The spacer is located outside the layer of pressure-sensitive resistor between the base films and used for forming the gap. The projection is located on an outer surface of one of the base films in order to decrease the lowest pressure that can be detected by the pressure sensor. The contact state between the layer of pressure-sensitive resistor and one of the electrodes varies to vary the resistance between the electrodes when a pressure acts on the projection.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT

The present invention will be described in detail with reference to various embodiments.

First Embodiment

Figure 1:
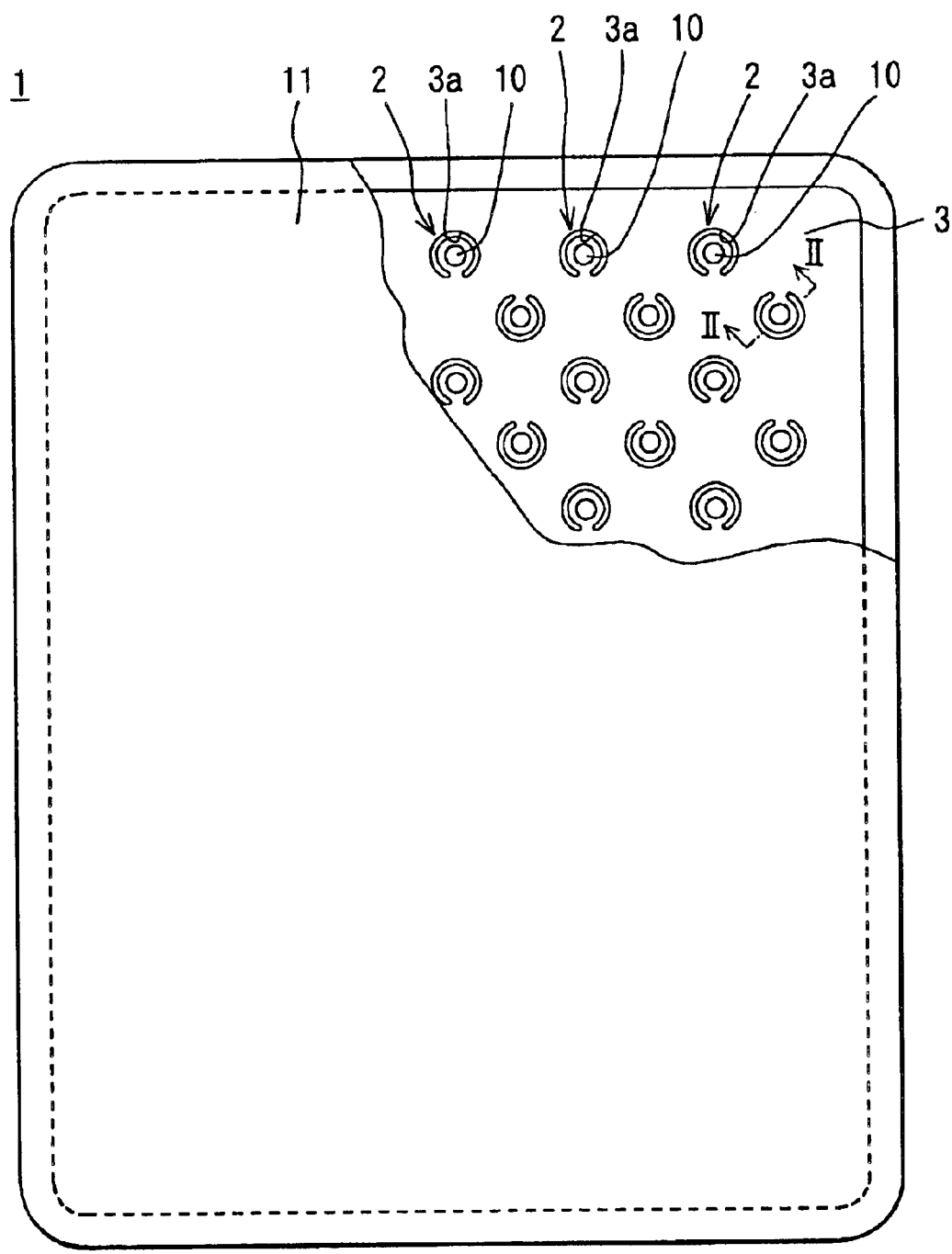
FIG. 1 is a schematic plan view of a pressure sensor sheet according to a first embodiment of the present invention, showing the arrangement of pressure sensors.
Figure 2:
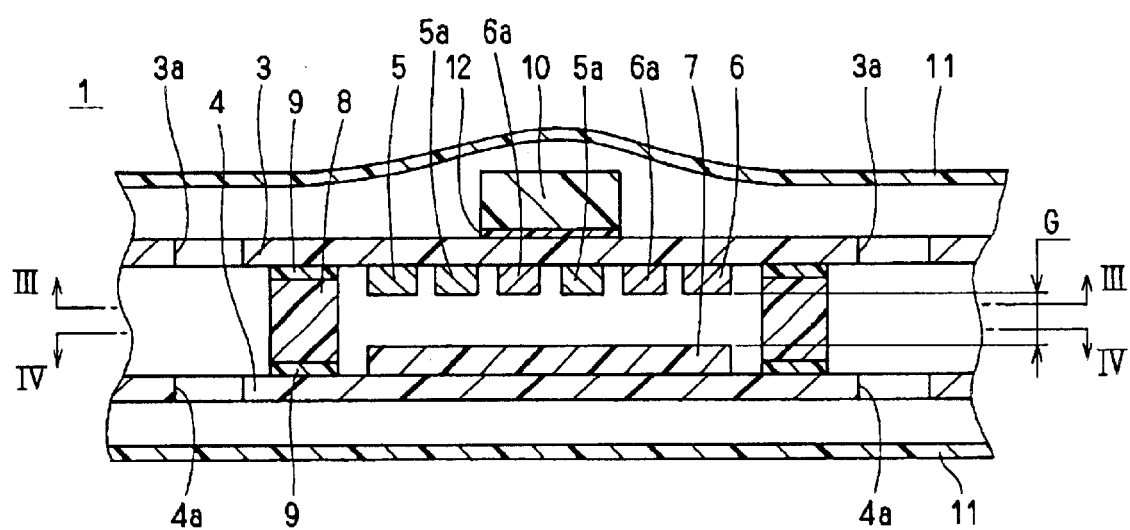
FIG. 2 is a partial schematic cross-sectional view of the pressure sensor sheet according to the first embodiment taken along the line II—II in FIG. 1.
Figure 3:
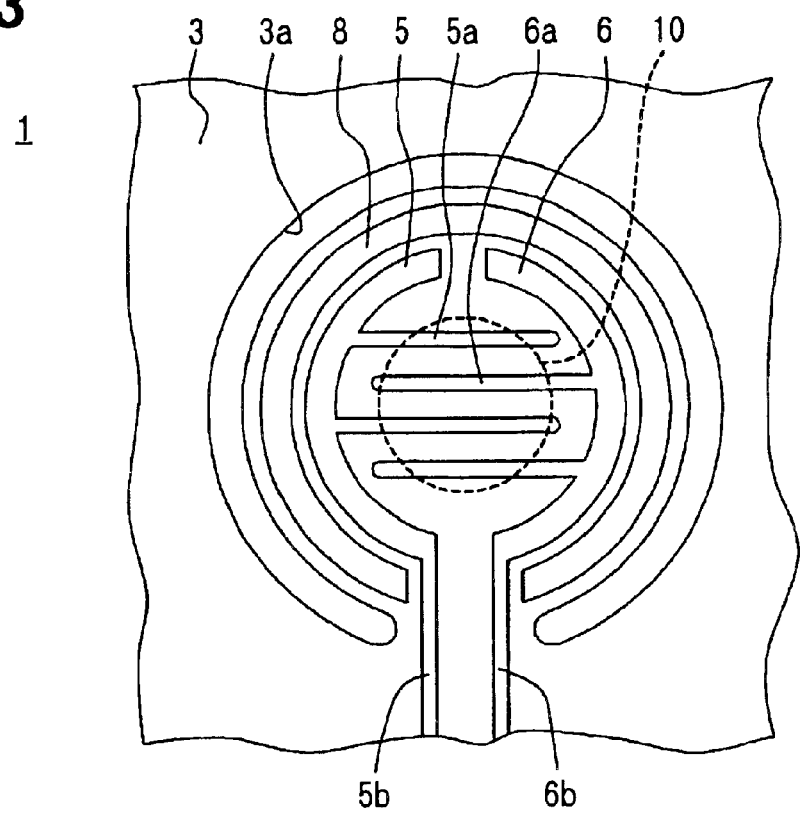
FIG. 3 is a partial schematic cross-sectional view of the pressure sensor sheet according to the first embodiment taken along the line III—III in FIG. 2.
Figure 4:
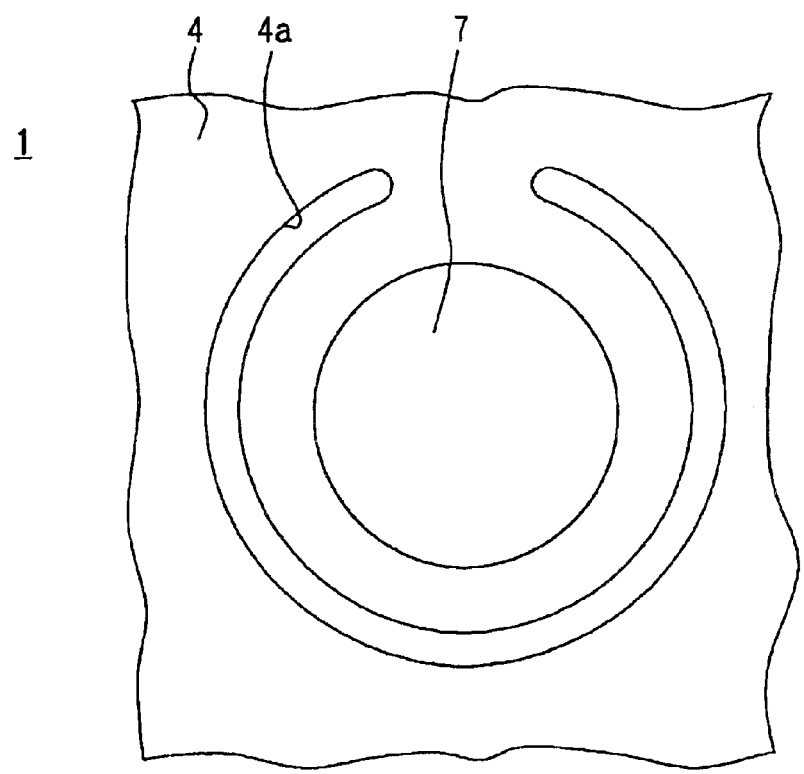
FIG. 4 is a schematic partial cross-sectional view of the pressure sensor sheet according to the first embodiment taken along the line IV—IV in FIG. 2.

As shown in FIG. 1, a pressure sensor sheet 1 according to a first embodiment of the present invention includes a plurality of pressure sensors 2. In FIG. 1, a part of a cover film 11 is omitted to show the pressure sensors 2. As shown in FIGS. 2 to 4, each of the pressure sensors 2 has a "shorting bar" structure. As shown in FIG. 2, each of the pressure sensors 2 includes: first and second base films 3, 4; first and second electrodes 5, 6, which are located between the base films 3, 4; first and second leads 5b, 6b, which are respectively electrically connected to the first and second electrodes 5, 6; a layer of pressure-sensitive resistor 7, which is arranged to have a predetermined gap G from the electrodes 5, 6; a spacer 8, which is located between the base films 3, 4 to form the gap G; and a projection 10, or a pointer 10, which is located on the outer surface of the first base films 3.

As shown in FIG. 3, the electrodes 5, 6 are comb-shaped and located on the inner surface of the first base film 3. The first and second electrodes 5, 6 respectively include first and second comb-tooth electrodes 5a, 6a, which are shorting bars. The first and second electrodes 5, 6 are respectively electrically connected to an outside circuit through the first and second leads 5b, 6b. The electrodes 5, 6, and the leads 5b, 6b are made of silver and formed by screen printing a paste including silver particles on the inner surface of the first base film 3 in the shape shown in FIG. 3.

The pressure-sensitive resistor 7 is located on the inner surface of the second base film 4, as shown in FIG. 4. The pressure-sensitive resistor 7 is disk-shaped and has an outer diameter that is substantially equal to that of a circle defined by the electrodes 5, 6. The pressure-sensitive resistor 7 is arranged to face the electrodes 5, 6. The pressure-sensitive resistor 7 is made of a material that is formed by dispersing carbon into a thermosetting resin and formed by screen printing the material on the inner surface of the second base film 4 in the shape shown in FIG. 4 in the same manner as in the electrodes 5, 6.

The spacer 8 is substantially C-shaped and located outside the electrodes 5, 6 and the pressure-sensitive resistor 7 to surround the electrodes 5, 6 and the pressure-sensitive resistor 7 in order to form the gap G between the electrodes 5, 6 and the pressure-sensitive resistor 7. The spacer 8 is made of a resin film and has been fixed to the base films 3, 4 with a thermosetting adhesive 9 therebetween.

The pointer 10 is disk-shaped and made of a rubber or a resin. The pointer 10 has been fixed to the outer surface of the first base film 3 with a thermosetting adhesive 12 therebetween. As shown in FIG. 3, the pointer 10 has been coaxially stacked above the circle defined by the electrodes 5, 6. Therefore, the pointer 10 is located right above an area that is substantially surrounded by the spacer 8. The first and second base films 3, 4 respectively have first and second slits 3a, 4a. Each of the slits 3a, 4a is substantially C-shaped and located outside the spacer 8 to surround the spacer 8. The slits 3a, 4a are formed by, for example, punching after the base films 3, 4 are integrated together by bonding with the spacer 8 therebetween.

As shown in FIG. 2, first and second cover films 11 are respectively located on the outer surface of the first base film 3 and the outer surface of the second base film 4. The cover films 11 are made of a flexible material such as polyurethane and hermetically seal the base films 3, 4 to prevent the ambient moisture and dust from entering the pressure sensors 2.

Next, the assembling method of the pressure-sensitive sheet 1 according to the first embodiment will be briefly explained. First, a paste including silver particles are screen printed on a first base film 3 to form first and second electrodes 5, 6, which respectively include comb-tooth electrodes 5a, 6a. At that time, first and second leads 5b, 6b are simultaneously formed.

Then, a material that has been formed by dispersing carbon into a thermosetting resin is screen printed on a second base film 4 to form pressure-sensitive resistors 7. Subsequently, the base films 3, 4 are stacked with spacers 8 therebetween. The stacking is implemented such that the electrodes 5, 6 and the pressure-sensitive resistors 7 face each other and the spacers 8 become located outside the pressure-sensitive resistors 7. Thin layers of a thermosetting adhesive 9 have been formed on both surfaces of the spacer 8, as shown in FIG. 2. Next, a stacked body that is essentially made up of the first base film 3, the spacers 8, and the second base film 4 is heated and pressed using a thermo compression bonding machine. With the heating and pressing, the stacked body is integrated with the thermosetting adhesive 9 formed on both surfaces of the spacers 8.

Then, first and second slits 3a, 4a are formed using a punching machine. Next, pointers 10 are fixed to the outer surface of the first base film 3 at the positions where pressure sensors 2 are formed using an adhesive 12. Finally, the integrated stacked body is hermetically sealed by first and second cover films 11 to complete a pressure sensor sheet 1 according to the first embodiment.

In the pressure sensor sheet 1 according to the first embodiment, the projection 10, or the pointer 10, has been formed on the outer surface of the first base film 3 at the positions where pressure sensors 2 are formed. When a pressure is exerted from above a pressure sensor 2 in the pressure sensor sheet 1, the pressure acts on the first base film 3 of the pressure sensor 2 through the pointer 10 of the pressure sensor 2. Therefore, the surface pressure that acts on the first base film 3 becomes higher than that of proposed pressure sensors that do not include any pointer 10, so the first base film 3 deforms more than those in the proposed pressure sensors. Thus, it is possible to decrease the detectable lowest pressure more than that of the proposed pressure sensors.

Figure 5:
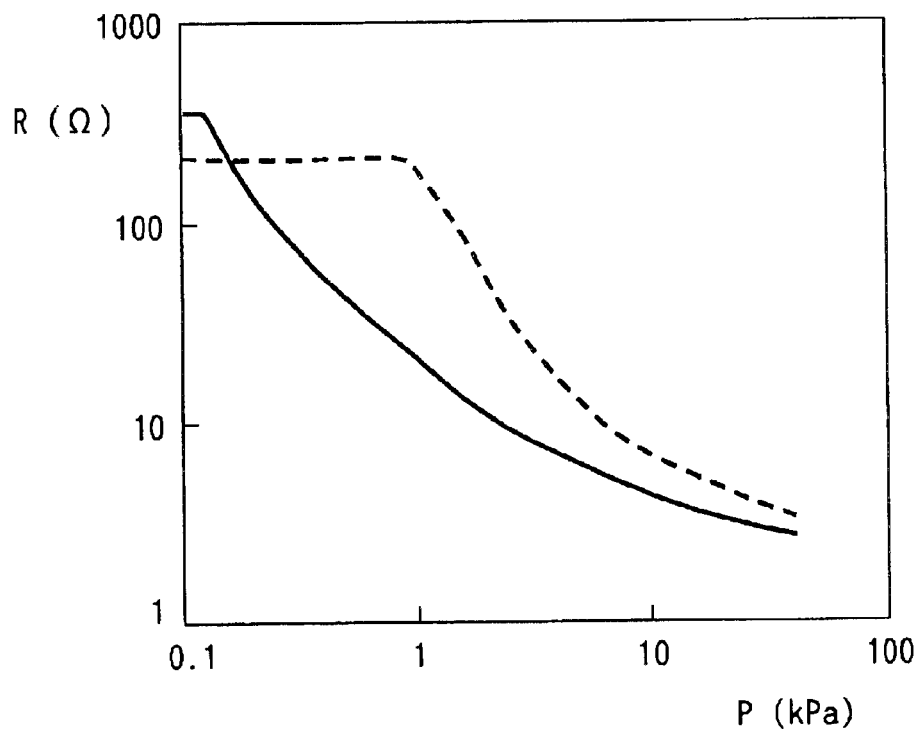
FIG. 5 is a graph that shows the correlation between the resistance between a pair of electrodes and the surface pressure exerted on one of the pressure sensors included in the pressure sensor sheet according to the first embodiment.

FIG. 5 is a graph that shows the correlation between the resistance R ($\Omega$) between a pair of electrodes and the surface pressure P (kPa) exerted on one of the pressure sensors included in the pressure sensor sheet according to the first embodiment. In FIG. 5, the solid curve represents the correlation in one of the pressure sensors that are included in the pressure sensor sheet according to the first embodiment and have a pointer 10, and the dotted curve represents the correlation in a proposed pressure sensor that does not have any pointer 10.

As clearly understood from FIG. 5, the resistance R is constant when the surface pressure P is below about 0.8 kPa in the proposed pressure sensor. That is, the detectable lowest pressure is 0.8 kPa. In contrast, the resistance R is constant when the surface pressure P is below about 0.15 kPa in the pressure sensor according to the first embodiment. That is, the detectable lowest pressure is 0.15 kPa. Therefore, it is possible to drastically decrease the detectable lowest pressure in the pressure sensor according to the first embodiment. Thus, it is possible to precisely acquire various living body information of a sleeper.

In the pressure sensor sheet 1 according to the first embodiment, the slits 3a, 4a have been formed in the base films 3, 4 outside the spacers 8 to surround the spacers 8. In proposed pressure sensor sheets, the base films complexly deforms to locally stretch the proposed pressure sensor sheet when in use, that is, when a sleeper lies on an article in which the proposed pressure sensor sheet has been placed. When the proposed pressure sensor sheet is locally stretched, the contact state between the pressure-sensitive resistors 7 and the electrodes 5, 6 varies.

As a result, the detection precision of the pressure sensors 2 lowers. For example, there may be a problem that precise detection of the living body information of a sleeper becomes difficult when a false output is generated by the local stretching of the proposed pressure sensor sheet even though no pressure due to a sleeper acts on the pressure sensors of the proposed pressure sensor sheet. In contrast, in the pressure sensor sheet 1 according to the first embodiment, the slits 3a, 4a prevent the tensile force from being transmitted to the pressure sensors 2 even when the pressure sensor sheet 1 is locally stretched. Because of the slits 3a, 4a, which surround the spacers 3, it is possible to permit each of the pressure sensors 2 to function like a discrete pressure sensor. Therefore, it is to provide a pressure sensor sheet 1 that has preferably high detection precision eliminating the influence of the tensile force on the contact state between the pressure-sensitive resistors 7 and the electrodes 5, 6.

Second Embodiment

Figure 6:
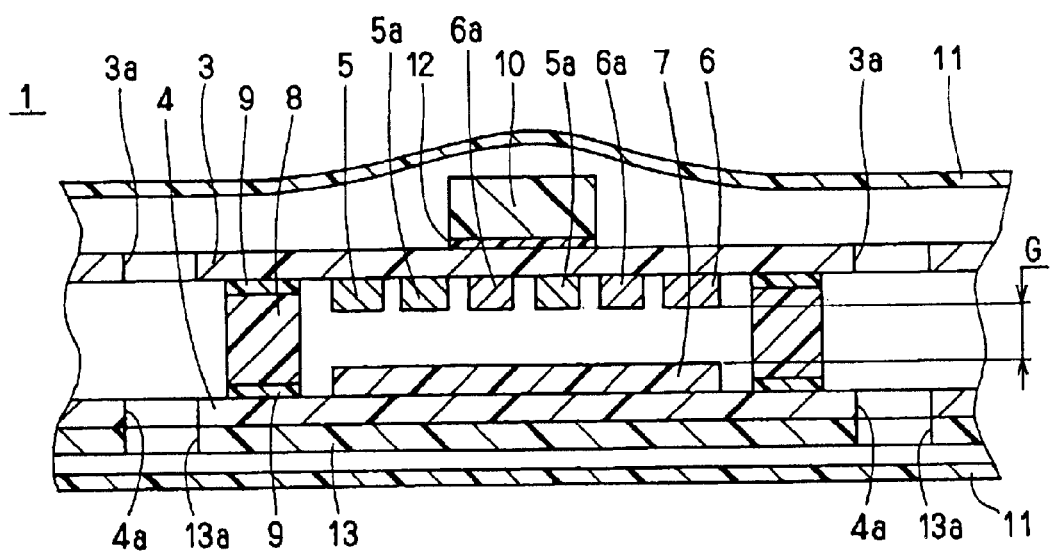
FIG. 6 is a partial schematic cross-sectional view of a pressure sensor sheet according to a second embodiment.

As shown in FIG. 6, a pressure sensor sheet 1 according to a second embodiment of the present invention has a structure in which a reinforcing sheet 13 has been added to the structure of the pressure sensor sheet 1 according to the first embodiment shown in FIG. 2. The reinforcing sheet 13 is made of a material having a rigidity or a elastic modulus higher than the second base film 4 of FIG. 2 and has substantially the same shape as the second base film 4. As illustrated in FIG. 6, the reinforcing sheet 13 has been bonded to the outer surface of a second base film 4. The reinforcing sheet 13 has slits 13a at the positions corresponding to first and second slits 3a, 4a of first and second base films 3, 4.

In the proposed pressure sensor sheet, the base films are thinned in order to precisely detect the load variation based on the minute local movement of a subject and to make the subject unconscious of the existence of the pressure sensor sheet. Therefore, the output characteristics of the pressure sensor vary and become unstable depending on the type and the rigidity of an article in which the proposed pressure sensor sheet is placed. That is, the output of the pressure sensor differs from an article to an article in which the proposed pressure sensor sheet is placed. As a result, there is a problem that precise detection of the living body information of a sleeper becomes difficult.

In the pressure sensor sheet 1 according to the second embodiment, the rigidity of the second base film 4 is enhanced by reinforcing the second base film 4 using the reinforcing sheet 13. Therefore, the deformability of the base films 3, 4 when a pressure acts on the pressure sensor sheet 1, or the correlation between the gap G between the pressure-sensitive resistors 7 and the electrodes 5, 6 and the pressure, can be constant irrespective of the specifications such as softness of an article in which the pressure sensor sheet is placed. As a result, it is to provide a pressure sensor sheet 1 that has preferably high detection precision preventing the output of the pressure sensor sheet 1 from differing from an article to an article in which the pressure sensor sheet is placed.

In the pressure sensor sheet 1 according to the second embodiment, the reinforcing sheet 13 has substantially the same shape as the second base film 4. That is, the reinforcing sheet 13 is a single sheet. Instead, a plurality of sheets made of the same material used for the reinforcing sheet 13 may be formed to have the same shape as the pressure sensors 2, that is, the shape surrounded by the slits 3a, 4a, and bonded to the second base film 4 at the areas surrounded by the slits 3a, 4a.

Third Embodiment

Figure 7:
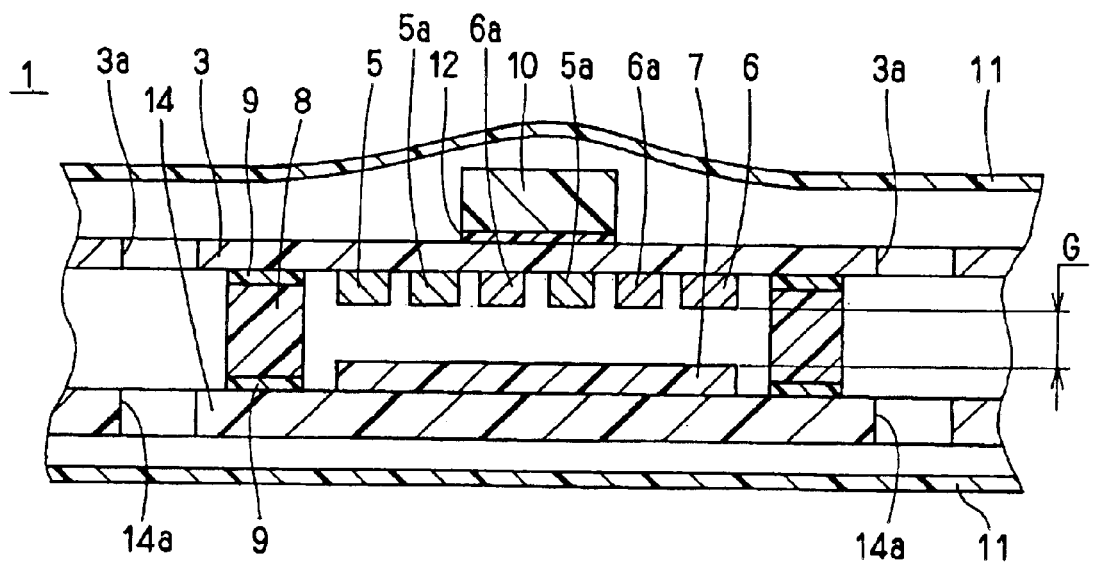
FIG. 7 is a partial schematic cross-sectional view of a pressure sensor sheet according to a third embodiment.

In the pressure sensor sheet 1 according to the first embodiment shown in FIG. 2, the first and second base films have the same rigidity or elastic modulus. In contrast, as shown in FIG. 7, a pressure sensor sheet 1 according to a third embodiment of the present invention has first and second base films 3, 14 that are different in rigidity or elastic modulus. More specifically, the second base film 14 is made of a material that has a rigidity or elastic modulus higher than that of the first base film 3. Other than that, the rigidity of the second film 14 may be increased by thickening the second film. Even in that case, the same effects are obtained.

In the pressure sensor sheet 1 according to the third embodiment as well, the rigidity of the second base film 14 has been enhanced in comparison with the first base film 3. Therefore, the deformability of the base films 3, 14 when a pressure acts on the pressure sensor sheet 1, or the correlation between the gap G between the pressure-sensitive resistors 7 and the electrodes 5, 6 and the pressure, can be constant irrespective of the specifications such as softness of an article in which the pressure sensor sheet is placed. As a result, it is to provide a pressure sensor sheet 1 that has preferably high detection precision preventing the output of the pressure sensor sheet 1 from differing from an article to an article in which the pressure sensor sheet is placed.

In addition, the second base film 14 itself has a high rigidity, so no reinforcing sheets 13 are required. Therefore, it is possible to prevent the number of parts and the number of production steps from increasing.

Fourth Embodiment

Figure 8:
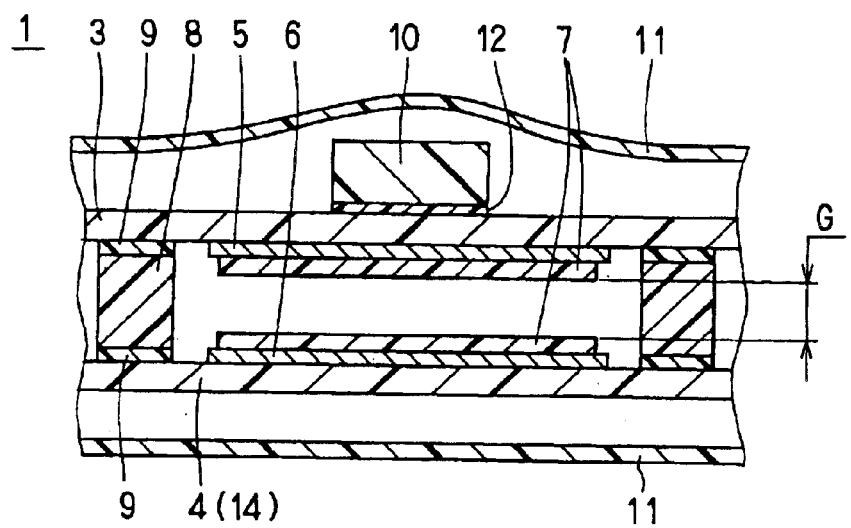
FIG. 8 is a partial schematic cross-sectional view of a pressure sensor sheet according to a fourth embodiment.

As shown in FIG. 8, a pressure sensor sheet 1 according to a fourth embodiment of the present invention is different in the arrangement of the electrodes 5, 6 and the pressure-sensitive resistor 7 from the pressure sensor sheets 1 according to the above embodiments. In the pressure sensor sheet 1 of FIG. 8, first and second base films 5, 6 are respectively located on first and second base films 3, 4 (14). In addition, first and second pressure-sensitive resistors 7 are respectively located on the first and second base films 3, 4 (14) with a gap G therebetween, as illustrated in FIG. 8. With the above structure, when a pressure acts on the pressure sensor sheet 1, the contact state between the first and second pressure-sensitive resistors 7 to vary the resistance between the first and second base films 5, 6. In the pressure sensor sheet 1 according to the fourth embodiment as well, the same effects as in the pressure sensor sheets 1 according to the first to third embodiments are obtained.

Other Embodiments

In the pressure sensor sheets 1 according to the first to fourth embodiments, the electrodes 5, 6 are formed by screen printing a paste including silver particles. Alternatively, the electrodes 5, 6 may be formed by plastering the base films 3, 4 (14) with conductive metal foils and patterning the foils into predetermined shapes by etching.

In the pressure sensor sheets 1 according to the first to fourth embodiments, the spacers 8 are made of a resin film. However, the spacers 8 may be formed using a thermosetting adhesive alone. In that case, spacers can be formed by screen printing the thermosetting adhesive onto one of the base films 3, 4 (14), so the number of the steps for manufacturing the pressure sensor sheet can be reduced.

In the pressure sensor sheets 1 according to the first to fourth embodiments, each of the pressure sensors 2 is equipped with a discrete pointer 10. Instead, a cluster of pointers 10 may be formed by linking the pointers 10 with a thin sheet and bonded to the first base film 3. The step of bonding the pointers 10 to the first base film 3 can be simplified with the cluster of pointers 10. In that case, the cluster may include all the pointers 10 needed for a pressure sensor sheet or a plurality of the clusters may be used for a pressure sensor sheet. The slits 3a, 4a are formed by punching after the cluster is bonded to the first base film 3.

In the pressure sensor sheets 1 according to the first to fourth embodiments, each of the pressure sensors 2 is equipped with a pair of electrodes 5, 6. Alternatively, each of the pressure sensors 2 may be equipped with a plurality of pairs of electrodes such that each pair can function as a discrete pressure-detecting unit. In that case, each of the pressure sensors 2 includes a plurality of discrete pressure-sensing units, so it is possible to increase the number of pressure-detecting points per unit area. With the above pressure sensor sheets 1, it becomes possible to accurately detect the position of a sleeper in addition to living body information such as respiration and pulse.

In the pressure sensor sheets 1 according to the first to fourth embodiments, the two surfaces of each of the spacers 8 that face the base films 3, 4 are located outside the electrodes 5, 6 and have been connected to the base film 3, 4 without the electrodes 5, 6 therebetween. However, the two surfaces of each of the spacers 8 that face the base films 3, 4 may be connected to the base film 3, 4 with any of the electrodes 5, 6 therebetween in order to stabilize the gap G.

What is claimed is:

1. A pressure sensor comprising:
    a pair of base films;
    a plurality of electrodes, which are located between the base films;
    a layer of pressure-sensitive resistor, which is located between the base films to be distant from one of the electrodes by a predetermined gap;
    a spacer, which is located outside the layer of pressure-sensitive resistor between the base films and used for forming the gap; and
    a projection, which is located on an outer surface of at least one of the base films in order to decrease the lowest pressure that can be detected by the pressure sensor, wherein a contact state between the layer of pressure-sensitive resistor and one of the electrodes varies to vary a resistance between the electrodes when a pressure acts on the projection.

2. The pressure sensor according to claim 1, wherein the projection is located right above an area that is substantially surrounded by the spacer.

3. The pressure sensor according to claim 2, wherein the projection is made of a rubber or a resin.

4. The pressure sensor according to claim 1, wherein a surface of the spacer that face one film out of the base films is connected to the one film with one of the electrodes therebetween in order to stabilize the predetermined gap.

5. The pressure sensor according to claim 1, wherein each of the base film has a slit that is located outside the spacer to surround the spacer.

6. A pressure sensor comprising:
    first and second base films;
    a pair of electrodes, which are located between the base films;
    a layer of pressure-sensitive resistor, which is located between the base films to be distant from one of the electrodes by a predetermined gap;
    a spacer, which is located outside the layer of pressure-sensitive resistor between the base films and used for forming the gap; and
    a reinforcing sheet, which is made of a material having a rigidity or a elastic modulus equal to or higher than the base films and located on an outer surface of the second base film such that a deformability of the first base film when a pressure acts on the first base film becomes substantially constant irrespective of specifications of an article in which the pressure sensor is placed, wherein a contact state between the layer of pressure-sensitive resistor and one of the electrodes varies in response to the pressure to vary a resistance between the electrodes.

7. The pressure sensor according to claim 6 further comprising a projection, which is located on at least an outer surface of one of the base films in order to decrease the lowest pressure that can be detected by the pressure sensor.

8. The pressure sensor according to claim 7, wherein the projection is located right above an area that is substantially surrounded by the spacer.

9. The pressure sensor according to claim 8, wherein the projection is made of a rubber or a resin.

10. The pressure sensor according to claim 6, wherein a surface of the spacer that face one film out of the base films is connected to the one film with one of the electrodes therebetween in order to stabilize the predetermined gap.

11. The pressure sensor according to claim 6, wherein each of the base film has a slit that is located outside the spacer to surround the spacer.

12. A pressure sensor comprising:
    first and second base films;
    a plurality of electrodes, which are located between the base films;
    a layer of pressure-sensitive resistor, which is located between the base films to be distant from one of the electrodes by a predetermined gap; and
    a spacer, which is located outside the layer of pressure-sensitive resistor between the base films and used for forming the gap,
    wherein the second base film has a rigidity or an elastic modulus higher than the first base film such that a deformability of the first base film when a pressure acts on the first base film becomes substantially constant irrespective of specifications of an article in which the pressure sensor is placed and wherein a contact state between the layer of pressure-sensitive resistor and one of the electrodes varies in response to the pressure to vary a resistance between the electrodes.

13. The pressure sensor according to claim 12 further comprising a projection, which is located on an outer surface of one of the base films in order to decrease the lowest pressure that can be detected by the pressure sensor.

14. The pressure sensor according to claim 13, wherein the projection is located right above an area that is substantially surrounded by the spacer.

15. The pressure sensor according to claim 14, wherein the projection is made of a rubber or a resin.

16. The pressure sensor according to claim 12, wherein a surface of the spacer that face one film out of the base films is connected to the one film with one of the electrodes therebetween in order to stabilize the predetermined gap.

17. The pressure sensor according to claim 12, wherein each of the base film has a slit that is located outside the spacer to surround the spacer.

* * * * *